(12) United States Patent
Weser et al.

(10) Patent No.: US 9,034,056 B2
(45) Date of Patent: May 19, 2015

(54) FOAM DYEING AGENT FOR KERATINOUS FIBERS WITH IMPROVED COLOR UPTAKE

(71) Applicant: Henkel AG & Co. KGaA, Dusseldorf (DE)

(72) Inventors: Gabriele Weser, Neuss (DE); Ulrike Schumacher, Duesseldorf (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 14/206,543

(22) Filed: Mar. 12, 2014

(65) Prior Publication Data

US 2014/0190999 A1    Jul. 10, 2014

Related U.S. Application Data

(63) Continuation of application No. PCT/EP2012/068217, filed on Sep. 17, 2012.

(30) Foreign Application Priority Data

Sep. 19, 2011  (DE) .......................... 10 2011 082 918

(51) Int. Cl.
| | | |
|---|---|---|
| *A61Q 5/10* | (2006.01) | |
| *A61K 8/04* | (2006.01) | |
| *A61K 8/42* | (2006.01) | |
| *A61K 8/36* | (2006.01) | |
| *B65D 83/14* | (2006.01) | |

(52) U.S. Cl.
CPC . *A61K 8/046* (2013.01); *A61K 8/42* (2013.01); *A61Q 5/10* (2013.01); *A61K 8/361* (2013.01); *B65D 83/752* (2013.01)

(58) Field of Classification Search
CPC ........... A61Q 5/10; A61K 8/42; A61K 8/361; A61K 8/046; B65D 83/752; A45D 2019/0066
USPC ....................... 8/405, 525, 580; 132/202, 208
See application file for complete search history.

(56) References Cited

U.S. PATENT DOCUMENTS

| 2004/0037786 A1 | 2/2004 | Birkel et al. | |
|---|---|---|---|
| 2007/0251025 A1* | 11/2007 | Errey et al. | ......... 8/405 |
| 2012/0192889 A1* | 8/2012 | Schmelz et al. | ......... 132/208 |

FOREIGN PATENT DOCUMENTS

| EP | 1374837 A1 | 1/2004 |
|---|---|---|
| EP | 2277600 A1 | 1/2011 |

OTHER PUBLICATIONS

STIC Search Report dated May 21, 2014.*
PCT International Search Report (PCT/EP2012/068217) dated Feb. 8, 2013.
www.gnpd.com; Database GNPD [Online] Mintel; "Colour Creme Gloss & Vive Pro Hydra-Gloss Shampoo Bonus Pack", XP002706285; pp. 1-4; Nov. 2008.
www.gnpd.com; Database GNPD [Online] Mintel; "Color Shampoo 304", XP002706286; Apr. 2003; pp. 1-2.

* cited by examiner

*Primary Examiner* — Eisa Elhilo
(74) *Attorney, Agent, or Firm* — Steven L. Nichols; Van Colt, Bagley, Cornwall & McCarthy P.C.

(57) ABSTRACT

The present application provides preparations for changing the color of keratinic fibers, containing in a cosmetically acceptable carrier, at least one color-changing agent, at least one soap, at least one non-ionic surfactant of formula (I),

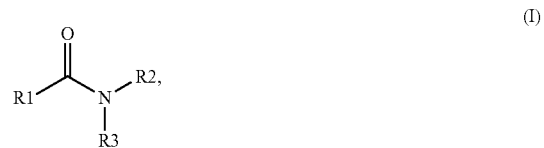

(I)

in which R1 denotes an alkyl or alkenyl residue having 5 to 21 carbon atoms, R2 denotes a C2-C4 monohydroxyalkyl residue, and R3 denotes hydrogen, a C1-C4 alkyl residue or a C2-C4 monohydroxyalkyl residue, and at least one propellant wherein the preparation is in the form of a foam, and a proportion of gas in the foam is at least 50% by volume.

20 Claims, No Drawings

FOAM DYEING AGENT FOR KERATINOUS FIBERS WITH IMPROVED COLOR UPTAKE

RELATED APPLICATIONS

The present specification is a U.S. continuation patent application under 35 U.S.C. 111(a) and claims the right of priority under 35 U.S.C. 365 to international patent Application No. PCT/EP2012/068217, filed Sep. 17, 2012, entitled "FOAM DYEING AGENT FOR KERATINOUS FIBRES WITH IMPROVED COLOUR UPTAKE" which claims benefit of German application No.: 102011082918.0, filed Sep. 19, 2011, these applications are herein incorporated by reference in their entirety.

FIELD OF THE INVENTION

The present invention generally relates to agents in foam form and to methods for changing the color of keratin-containing fibers, containing a specific combination of surfactants. The invention also relates to a corresponding kit comprising a plurality of components for changing the color of keratin-containing fibers.

BACKGROUND OF THE INVENTION

Various methods are used for changing the color of human hair. As a general rule, either substantive dyes or oxidation dyes, which are formed by the oxidative coupling of one or more developer components with one another or with one or more coupler components, may be used to color human hair. These coupler and developer components are known as oxidation dye precursors. The colors obtained with oxidation dyes may be referred to as permanent or semipermanent colors. Oxidative lightening methods, in which natural or synthetic dyes in the hair fiber are destroyed by oxidation, causing the color to be removed, may be used for lightening or bleaching.

In order to accelerate the reaction during the oxidation process, oxidative coloring and lightening agents mostly have an alkaline pH, which may be adjusted using alkalizing agents such as alkanol amines, ammonia or inorganic bases. Although ammonia in particular allows for good coloring results, it also presents disadvantages for the user because of its odor and its irritation potential for skin and mucous membranes. For that reason, efforts are intensifying to develop high-performance oxidative coloring and lightening agents that dispense with the use of ammonia.

These agents mostly contain hydrogen peroxide as the oxidizing agent. As hydrogen peroxide is not sufficiently stable in storage in the alkaline pH range, oxidative coloring and/or lightening agents may include two components, which are mixed together immediately before use. The problem posed by this approach is firstly that of homogeneously mixing the two components. This could be solved by means of correspondingly readily miscible components, in particular low-viscosity liquids; however, the application mixture must be sufficiently viscous for it to be easily applied to the hair and not to drip or run off during the contact time. The problem with commercial high-viscosity cream or gel applications is that applying them to the hair is often a laborious and time-consuming process. Additionally, an uneven application can easily lead to inhomogeneous or even patchy coloring or bleaching results. For that reason, there has been no shortage of attempts to develop other presentation forms.

Some alternatives have included applying lower-viscosity coloring or lightening agents to the hair using special applicator systems or applying coloring agents as a foam. Application as a foam, in particular as an aerosol foam, which are foamed by propellant gases when the product is dispensed, is widespread.

A foam application has advantages over gel or cream applications in terms of applying and distributing the color-changing agents on the user's hair. However, these advantages are countered by disadvantages concerning coloring capacity, in particular with regard to color uptake, which is offset either by means of longer contact times during application or by higher dye or lightening agent concentrations in the preparations. A further problem relating to foam application relates to the stabilization of the foams. Foam stability in particular has a major influence on both the performance and the ease of application of the agents. Foam stability is negatively influenced in particular by the presence of large amounts of salts and dyes or dye precursors. The ideal foams provide a solid, stable foam that leaves behind a soft feel and breaks down slowly on the hair. Frequently, however, the dispensed foams have poor stability and rapidly collapse and liquefy, leaving behind a low-viscosity, dripping solution. The foam should also wet the hair thoroughly and break down slowly to allow for a good color uptake.

Therefore, there is still a need for an easy-to-handle presentation form for oxidative hair color-changing agents, such as a permanent hair color agent or hair bleaching agent. This application form should allow a drip-free application and its performance should not be inferior to that of commercial cream or gel applications, in particular with regard to lightening and coloring capacity and fastness properties. The coloring results should be outstanding in terms of intensity, gray coverage and shine, they should have superb care properties and a long life, including in respect of external influences such as hair washing.

Accordingly, the present specification describes methods for using oxidative color-changing agents, in particular for foam application, such that the aforementioned disadvantages can be overcome. In particular, stable color-changing foams should be provided.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A preparation for changing the color of keratinic fibers, containing in a cosmetically acceptable carrier at least one color-changing agent and at least one soap, and at least one non-ionic surfactant of formula (I):

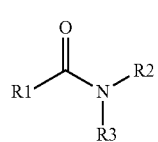

(I)

in which R1 denotes an alkyl or alkenyl residue having 5 to 21 carbon atoms, R2 denotes a $C_2$-$C_4$ monohydroxyalkyl residue, and R3 denotes hydrogen, a $C_1$-$C_4$ alkyl residue or a $C_2$-$C_4$ monohydroxyalkyl residue.

A method for changing the color of keratinic fibers, the method including applying at the same time, a preparation and an oxidizing agent preparation containing in a cosmetic carrier to the keratinic fibers. The preparation comprises at least one color-changing agent, at least one soap, and at least one non-ionic surfactant of formula (I). The oxidizing agent preparation comprises at least one oxidizing agent and a propellant. The preparation and the oxidizing agent preparation may be distributed uniformly over the fibers. The method also includes rinsing the preparation and the oxidizing agent preparation out of the fibers after a contact time of 10 to 45 minutes at a temperature of 20 to 45 degrees Celsius.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Oxidative color-changing agents containing a specific surfactant combination of soaps and non-ionic surfactants of the fatty acid alkanol amide type may produce extremely stable foams, which may allow for an easy and intense coloring of the fibers and may lead to outstanding color uptake on the fibers. The stability is maintained even with relatively high salt concentrations. These agents can be distributed very easily and evenly on the hair with the hands, making the agents easy to handle. Furthermore, the agents according to the present specification may allow for more intense coloring results, in particular with regard to intensity, and achieve significantly more lasting coloring results than hitherto known foam preparations. The foam application may allow for an excellent application effect. In particular because a homogeneous distribution is ensured, undesirably high local concentrations of the coloring or bleaching agent are avoided.

The present specification provides a preparation for changing the color of keratinic fibers, containing, in a cosmetically acceptable carrier:
  at least one color-changing agent;
  at least one soap; and
  at least one non-ionic surfactant of formula (I)

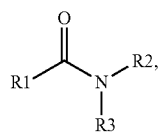

(I)

in which:
  R1 denotes an alkyl or alkenyl residue having 5 to 21 carbon atoms,
  R2 denotes a $C_2$-$C_4$ monohydroxyalkyl residue, and
  R3 denotes hydrogen, a $C_1$-$C_4$ alkyl residue or a $C_2$-$C_4$ monohydroxyalkyl residue.

As used in the present specification and in the appended claims, the term "keratin-containing," "keratinic fibers," or similar terminology may refer to wool, fur, feathers and in particular human hair. However, the coloring and lightening methods described herein in principle may also be used for application on other natural fibers, such as for example cotton, jute, sisal, linen, silk or modified natural fibers, such as for example regenerated cellulose, nitrocellulose, alkyl or hydroxyalkyl cellulose or acetyl cellulose.

The preparations according to the present specification may contain the ingredients in a cosmetically acceptable carrier. This cosmetic carrier is preferably aqueous, alcoholic or aqueous-alcoholic. An aqueous carrier may contain within the meaning of the present specification at least 40 wt. %, in particular at least 50 wt. %, of water. Within the meaning of the present specification aqueous-alcoholic carriers may refer to hydrous compositions containing 3 to 70 wt. % of a $C_1$ to $C_4$ alcohol, in particular ethanol or isopropanol. The agents according to the present specification may additionally contain further organic solvents, such as for example 4-methoxybutanol, ethyl diglycol, 1,2-propylene glycol, n-propanol, n-butanol, n-butylene glycol, glycerol, diethylene glycol monoethyl ether, and diethylene glycol mono-n-butyl ether, provided that they do not have an overly negative influence on foam forming and foam stability. Water-soluble organic solvents are preferred here. Preferred color-changing agents according to the present specification may be characterized in that they additionally contain a non-aqueous solvent, wherein preferred preparations according to the present specification may contain the solvent in a concentration from 0.1 to 30 wt. %, preferably in a concentration from 0.5 to 20 wt. %, most particularly preferably in a concentration from 1 to 10 wt. %, relative in each case to the preparation.

The preparation may contain at least one color-changing agent. Preferred color-changing agents may be selected from oxidation dye precursors, substantive dyes and peroxo salts.

In a preferred example, the color-changing preparation may contain at least one oxidation dye precursor as the color-changing agent. The preparation preferably contains one or more developer components and optionally one or more coupler components.

At least one compound from the group which is formed from p-phenylenediamine, p-toluoylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, and the physiologically acceptable salts thereof may be preferably selected as the developer component.

The developer components are preferably used in an amount from 0.005 to 20 wt. %, preferably 0.1 to 5 wt. %, in particular from 0.5 to 3.5 wt. %, relative in each case to the total weight of the preparation.

In the context of oxidative dyeing, coupler components may not develop significant color on their own and may need the presence of developer components. It is therefore preferable according to the present specification that if at least one developer component is used, then at least one coupler component is additionally used.

Coupler components that are preferred according to the invention are selected from 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol, 2,4-dichloro-3- aminophenol, 2-(2,4-diaminophenoxy)ethanol, 1,3-bis-(2,4-diaminophenoxy)propane, 1-methoxy-2-amino-4-(2-hydroxyethylamino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, resorcinol monomethyl ether, 2-methylresorcinol, 5-methylresorcinol, 2,5-dimethylresorcinol, 2-chlororesorcinol, 4-chlororesorcinol, pyrogallol, 1,2,4-trihydroxybenzene, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 2,6-dihydroxy-3,4-dimethylpyridine, 3,4-diaminopyridine, 2-(2-methoxyethyl)amino-3-amino-6-methoxypyridine, 2-(4'-methoxyphenyl)amino-3-aminopyridine, 1-naphthene, 2-methyl-1-naphthene, 2-hydroxymethyl-1-naphthene, 2-hydroxyethyl-1-naphthene, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, 2,3-dihydroxynaphthalene, 4-hydroxyindole, 6-hydroxyindole, 7-hydroxyindole, 4-hydroxyindoline, 6-hydroxyindoline, 7-hydroxyindoline, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine or mixtures of these compounds or physiologically acceptable salts thereof.

The coupler components may be preferably used in an amount from 0.005 to 20 wt. %, preferably 0.1 to 5 wt. %, in particular from 0.5 to 3 wt. %, relative in each case to the total weight of the preparation.

Developer components and coupler components may be used in approximately molar amounts to one another. Even if the molar use has proved convenient, a certain excess of individual oxidation dye precursors is not disadvantageous, such that developer components and coupler components may be in a molar ratio of 1:0.5 to 1:3, in particular 1:1 to 1:2.

In another example, the preparation contains at least one substantive dye as the color-changing agent. The substantive dye may be used for shading lightening agents or oxidation colors or may be included as the sole color-changing agent.

Substantive dyes may be dye molecules which attach directly to the substrate and require no oxidative process to develop the color. Examples of suitable substantive dyes are nitrophenylene diamines, nitroaminophenols, azo dyes, anthraquinones or indophenols. The substantive dyes are each preferably used in an amount from 0.001 to 20 wt. %, in particular 0.02 to 5 wt. % and particularly from 0.05 to 1.0 wt. %, relative in each case to the total weight of the color-changing preparation.

Preferred anionic substantive dyes may be the compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52, as well as tetrabromophenol blue and bromophenol blue.

Examples of preferred cationic substantive dyes are Basic Blue 7, Basic Blue 26, Basic Violet 2 and Basic Violet 14, Basic Yellow 57, Basic Red 76, Basic Blue 99, Basic Brown 16 and Basic Brown 17, Basic Yellow 87, Basic Orange 31 and Basic Red 51.

Examples of preferred non-ionic substantive dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

In another example, the preparation may contain at least one peroxo salt as the color-changing agent. Peroxo salts that may be suitable include ammonium persulfate, sodium persulfate, potassium persulfate and mixtures thereof.

The ready-to-use agent may preferably contain the peroxo salts in a proportion by weight from 1.0 to 25 wt. %, preferably 3 to 20 wt. % and in particular from 5 to 15 wt. %, relative in each case to the total weight of the preparation.

The preparation may contain at least one soap as another ingredient. The phrase "soap" may refer to salts of fatty acids. These fatty acids may have 8 to 22 carbon atoms and can on the one hand be branched or unbranched and on the other hand contain saturated or unsaturated alkyl chains.

Examples of suitable fatty acids may include saturated, unbranched fatty acids, such as octanoic acid (caprylic acid), nonanoic acid (pelargonic acid), decanoic acid (capric acid), undecanoic acid, dodecanoic acid (lauric acid), tridecanoic acid, tetradecanoic acid (myristic acid), pentadecanoic acid, hexadecanoic acid (palmitic acid), heptadecanoic acid (margaric acid), octadecanoic acid (stearic acid), nonadecanoic acid, eicosanoic acid (arachidic acid), docosanoic acid (behenic acid);

saturated, branched fatty acids, such as isooctanoic acid, isopalmitic acid, isostearic acid;

unsaturated, unbranched fatty acids, such as palmitoleic acid ((9Z)-hexadec-9-enoic acid), oleic acid ((9Z)-octadec-9-enoic acid), elaidic acid ((9E)-octadec-9-enoic acid), erucic acid ((13Z)-docos-13-enoic acid), linoleic acid ((9Z,12Z)-octadeca-9,12-dienoic acid), linolenic acid ((9Z,12Z,15Z)-octadeca-9,12,15-trienoic acid), elaeostearic acid ((9Z,11E,13E)-octadeca-9,11,13-trienoic acid), arachidonic acid ((5Z,8Z,11Z,14Z)-eicosa-5,8,11,14-tetraenoic acid).

The fatty acids of the soaps may be present in deprotonated form. Alkali metal ions, alkaline-earth metal ions and zinc ions may be suitable in particular as cationic counterions. Examples of preferred soaps may include the salts of fatty acids with alkali metal ions as counterions, in particular with sodium or potassium ions, particularly with sodium ions.

Particular alkali metal salts of branched and/or unsaturated fatty acids may be incorporated superbly well into the preparations as soaps, thereby contributing decisively to improving the color uptake.

Accordingly, in one example, a preparation may include a soap that is an alkali metal salt of an unsaturated and/or branched fatty acid having 8 to 22 carbon atoms.

An alkali metal salt of oleic acid is most particularly preferred. Accordingly, in one example, the preparation may be characterized in that the soap is an alkali metal salt of oleic acid.

In some examples, a certain proportion of soap is favorable in the preparations. For example, preparations according to the present specification may be characterized in that the soap(s) is/are included in a proportion from 0.1 to 6 wt. %, preferably from 0.5 to 5 wt. %, in particular from 1.0 to 4.5 wt. % and particularly preferably from 1.5 to 4.0 wt. %, relative in each case to the total weight of the preparation.

The preparation of the present specification may contain at least one non-ionic surfactant according to formula (I).

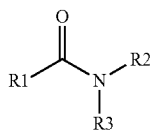

(I)

In non-ionic surfactants according to formula (I), R1 may denote an alkyl or alkenyl residue having 5 to 21 carbon atoms. Alkyl residues may refer to saturated hydrocarbon residues which optionally have branches. Alkenyl residues may refer to unsaturated hydrocarbon residues having one or more olefinic double bonds and additionally optionally branches.

Preferred examples of residues R1 include saturated, unbranched alkyl residues having 7 to 17 carbon atoms and unbranched alkenyl residues having one or two olefinic double bonds and 11 to 17 carbon atoms. In some examples, a mixture of various compounds of formula (I), in which the compounds differ from one another through differing residues R1 may be used as the surfactant. This can be advantageous in particular for the use of technical or natural products in which for production reasons the residue R1 derives from a mixture of different fatty acids.

The residue R2 of formula (I) may denote a $C_2$-$C_4$ monohydroxyalkyl residue. Examples of such residues are 2-hydroxyethyl ($CH_2CH_2OH$), 2-hydroxypropyl (2-hydroxy-2-methylpropyl; $CH_2CH(CH_3)OH$), 3-hydroxypropyl ($CH_2CH_2CH_2OH$), 1-hydroxyprop-2-yl ($CH(CH_3)CH_2OH$), 4-hydroxybutyl ($CH_2CH_2CH_2CH_2OH$), 3-hydroxybutyl ($CH_2CH_2CH(CH_3)OH$), 2-hydroxybutyl ($CH_2CH(CH_2CH_3)OH$), 1-hydroxybut-2-yl (3-hydroxy-1-methylpropyl; $CH(CH_3)CH_2CH_2OH$), 3-hydroxybut-2-yl (2-hydroxy-1-methylpropyl; $CH(CH_3)CH(CH_3)OH$), 1-hydroxybut-2-yl (1-(hydroxymethyl)propyl; $CH(CH_2CH_3)CH_2OH$), 3-hydroxy-2-methylpropyl ($CH_2CH(CH_3)CH_2OH$) and 1-hydroxy-2-methylprop-2-yl ($C(CH_3)_2CH_2OH$).

The residue R2 may preferably denote 2-hydroxyethyl, 2-hydroxypropyl (2-hydroxy-2-methylpropyl) and 1-hydroxy-2-methylprop-2-yl, particularly preferably 2-hydroxyethyl.

The residue R3 of formula (I) may denote hydrogen, a C1-C4 alkyl residue or a C2-C4 monohydroxyalkyl residue. Examples of a C1-C4 alkyl residue are methyl, ethyl, prop-1-yl, prop-2-yl (isopropyl), but-1-yl, but-2-yl and 2-methylprop-2-yl.

R3 may preferably denote hydrogen, methyl, 2-hydroxyethyl or 2-hydroxypropyl (2-hydroxy-2-methylpropyl), particularly preferably hydrogen or 2-hydroxyethyl and in particular hydrogen.

In a preferred example R2 may denote 2-hydroxyethyl and R3 may denote hydrogen (fatty acid monoethanolamide; fatty acid amide MEA). Examples include capramide MEA (R1=$C_9$ alkyl), lauramide MEA (R1=alkyl), myristamide MEA (R1=$C_{13}$ alkyl), palmitamide MEA (R1=$C_{15}$ alkyl), stearamide MEA (R1=$C_{17}$ alkyl), isostearamide MEA (R1=$C_{17}$ isoalkyl), oleamide MEA (R1=$C_{17}$ alkenyl), linoleamide MEA (R1=$C_{17}$ alkyldienyl), cocamide MEA (R1 derived from coconut fatty acids, approx. 42-53% $C_{11}$/13-22% $C_{13}$/6-10% $C_9$/7-11% $C_{15}$/4-10% $C_{17:1}$/5-9% $C_7$), palm kernel amide MEA (R1 derived from palm kernel fatty acids) and soyamide MEA (R1 derived from soya fatty acids, approx. 82% $C_{17}$/14% $C_{15}$/4% $C_{13}$).

In a preferred example R2 may denote 2-hydroxypropyl (2-hydroxy-2-methylpropyl) and R3 may denote hydrogen (fatty acid monoisopropanolamide; fatty acid amide MIPA). Examples are capramide MIPA, lauramide MIPA, myristamide MIPA, palmitamide MIPA, stearamide MIPA, isostearamide MIPA, oleamide MIPA, linoleamide MIPA, cocamide MIPA, palm kernel amide MIPA and soyamide MIPA.

In a preferred example R2 may denote 1-hydroxy-2-methylprop-2-yl and R3 may denote hydrogen (monoamide of fatty acids and 2-amino-2-methylpropan-1-ol; fatty acid amide AMP). Examples of this embodiment are capramide AMP, lauramide AMP, myristamide AMP, palmitamide AMP, stearamide AMP, isostearamide AMP, oleamide AMP, linoleamide AMP, cocamide AMP, palm kernel amide AMP and soyamide AMP.

In a further preferred example R2 may denote 2-hydroxyethyl and R3 may denote 2-hydroxyethyl (fatty acid diethanolamide; fatty acid amide DEA). Examples are capramide DEA, lauramide DEA, myristamide DEA, palmitamide DEA, stearamide DEA, isostearamide DEA, oleamide DEA, linoleamide DEA, cocamide DEA, palm kernel amide DEA and soyamide DEA.

In a further preferred example R2 may denote 2-hydroxypropyl and R3 may denote 2-hydroxypropyl (fatty acid diisopropanolamide; fatty acid amide DIPA). Examples are capramide DIPA, lauramide DIPA, myristamide DIPA, palmitamide DIPA, stearamide DIPA, isostearamide DIPA, oleamide DIPA, linoleamide DIPA, cocamide DIPA, palm kernel amide DIPA and soyamide DIPA.

In a further preferred example R2 may denote 2-hydroxyethyl and R3 may denote methyl (fatty acid (methyl)ethanolamide; fatty acid amide methyl MEA). Examples are capramide methyl MEA, lauramide methyl MEA, myristamide methyl MEA, palmitamide methyl MEA, stearamide methyl MEA, isostearamide methyl MEA, oleamide methyl MEA, linoleamide methyl MEA, cocamide methyl MEA, palm kernel amide methyl MEA and soyamide methyl MEA.

Most particularly preferably, R2 denotes 2-hydroxyethyl and R3 denotes hydrogen; compounds of formula (I) that are preferred in particular are cocamide MEA, lauramide MEA, palmitamide MEA and stearamide MEA. Examples of suitable commercial products are MACKAMIDE CMA (McINTYRE Group Ltd.), Galaxy 100 (Galaxy Surfactants Ltd.), Monamid CMA (Uniqema), Empilan CME (Huntsman) and Comperlan 100 (BASF) or Comperlan LM (BASF) or Nikkol PMEA (Nikko Chemicals) or Comperlan HS (BASF). Cocamide MEA is particularly preferred as the compound of formula (I).

To improve the foam stability and color uptake it may be advantageous to incorporate the non-ionic surfactants into the preparation in specific quantitative proportions. In another example, the preparations according to the present specification may be characterized in that the non-ionic surfactant of formula (I) is included in a proportion from 0.1 to 10 wt. %, preferably from 0.2 to 5 wt. %, in particular from 0.4 to 3.5 wt. % and particularly preferably from 0.6 to 2.5 wt. %, relative in each case to the total weight of the preparation.

Preparations containing potassium oleate and cocamide MEA are exceptionally preferred. Preparations containing potassium oleate and lauramide MEA are also exceptionally preferred.

Most particularly advantageous foam stabilities and color-changing results may be obtained by using soap(s) and non-ionic surfactants of formula (I) in a specific weight ratio to one another. Preparations that are particularly advantageous may be those in which soap(s) and non-ionic surfactants of formula (I) have a value of 8/1 to 1/3, preferably 5/1 to 1/2, particularly preferably 4.5/1 to 1/1 and in particular 4.0/1 to 1.2/1 for the weight ratio [sum of all soap(s)]/[sum of all non-ionic surfactants of formula (I)].

Preparations containing potassium oleate and cocamide MEA in the weight ratio of 8/1 to 1/3, preferably 5/1 to 1/2, particularly preferably 4.5/1 to 1/1 and in particular 4.0/1 to 1.2/1 may be exceptionally preferred.

Preparations containing potassium oleate and lauramide MEA in the weight ratio of 8/1 to 1/3, preferably 5/1 to 1/2, particularly preferably 4.5/1 to 1/1 and in particular 4.0/1 to 1.2/1 may be also exceptionally preferred.

The effect of the preparations may be further improved by adding further non-ionic surfactants. Particularly advantageous additional non-ionic surfactants may be non-ionic surfactants of the alkyl polyglucoside and (poly)alkoxylated fatty acid ester type.

Therefore, in a further preferred example, the preparation additionally contains at least one further, non-ionic surfactant, selected from alkyl polyglucosides and/or alkoxylated fatty acid esters.

As used in the present specification, "alkyl polyglucosides" may refer to compounds of formula (II)

$$R'-O-[G]_p \quad (II),$$

in which R' denotes an alkyl or alkenyl residue having 4 to 22 carbon atoms, G denotes a sugar residue having 5 or 6 carbon atoms and p denotes a number from 1 to 10.

The sugar residue G is derived from aldoses or ketoses having 5 or 6 carbon atoms, preferably from glucose.

The index value "p" in the general formula (II) indicates the degree of polymerization (DP), i.e. the distribution of mono- and polyglucosides, and denotes a number between 1 and 10. While "p" in the individual molecule is an integer number and the values p=1 to 6 may be assumed here, the value "p" for a particular alkyl polyglucoside is a calculated quantity determined by analysis. Alkyl polyglucosides having an average degree of oligomerization p of 1.1 to 3.0 may be preferably used. From an application-oriented perspective, alkyl polyglucosides having a degree of polymerization (i.e. the value p) below 1.7 and in particular between 1.2 and 1.4 may be preferred.

The alkyl residue R' may derive from primary alcohols having 4 to 11, preferably 8 to 10 carbon atoms. Examples include butanol, hexanol, octanol, decanol and undecanol as well as the technical mixtures thereof, such as are obtained for example in the hydrogenation of technical fatty acid methyl esters or during the hydrogenation of aldehydes from the Roelen oxo synthesis. Preference is given to alkyl polyglucosides with a chain length of $C_8$-$C_{10}$ (DP=1 to 3) which occur as the first flush in the separation by distillation of technical $C_8$-$C_{18}$ coconut fatty alcohol and which can be contaminated with a proportion of less than 6 wt. % of $C_{12}$ alcohol, as well as to alkyl polyglucosides based on technical $C_{9/11}$ oxo alcohols (DP=1 to 3).

The alkyl residue R' may further derive from primary alcohols having 12 to 22, preferably 12 to 14 carbon atoms. Examples include lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol as well as technical mixtures thereof, which can be obtained as described above. Alkyl polyglucosides based on hydrogenated $C_{12/14}$ coconut alcohol with a DP of 1 to 3 are preferred.

R' preferably denotes a coconut alkyl group, a stearyl group, a cetyl group, a lauryl group, mixtures of $C_8$-$C_{10}$ alkyl groups, mixtures of $C_{12/14}$ alkyl groups and/or mixtures thereof.

Alkyl polyglucosides that are particularly suitable may be sold under the INCI name Coco Glucoside and the trade name Plantacare 818 UP or under the INCI name Lauryl Glucoside and the trade name Plantacare 1200 UP.

It is preferable to use the alkyl polyglucosides in a proportion from 0.1 to 12 wt. %, preferably from 0.5 to 10 wt. %, in particular preferably from 1.0 to 9 wt. % and more preferably from 1.5 to 7.5 wt. %, relative in each case to the total weight of the preparation.

As used in the present specification and in the appended claims, the term "(poly)alkoxylated fatty acid esters may refer to compounds containing an ester of a fatty acid and containing a hydroxyl group that has been etherified with one or more alkoxy groups. The fatty acid esters are preferably fatty acid triglycerides whose fatty acids have at least one polyalkoxylated hydroxyl group. Particularly preferred fatty acid triglycerides are castor oil and hydrogenated castor oil. Polyalkoxylation mostly takes place with ethylene oxide, the degree of alkoxylation (i.e. the reacted number of mols of ethylene oxide per mol of hydroxyl group of the fatty acid ester) is preferably at least 20, better 40. Examples of (poly) alkoxylated fatty acid esters that are suitable according to the invention are sold under the INCI names PEG-2 Hydrogenated Castor Oil, PEG-5 Hydrogenated Castor Oil, PEG-7 Hydrogenated Castor Oil, PEG-10 Hydrogenated Castor Oil, PEG-25 Hydrogenated Castor Oil, PEG-30 Hydrogenated Castor Oil, PEG-40 Hydrogenated Castor Oil, PEG-50 Hydrogenated Castor Oil, PEG-54 Hydrogenated Castor Oil, PEG-60 Hydrogenated Castor Oil, PEG-35 Castor Oil, PEG-36 Castor Oil, PEG-40 Castor Oil, PEG-200 Castor Oil.

(Poly)alkoxylated fatty acid esters that are particularly suitable according to the invention may be available under the INCI name PEG-40 Hydrogenated Castor Oil and the trade name Cremophor CO 40 (BASF) or under the INCI name PEG-60 Hydrogenated Castor Oil and the trade name Cremophor CO 60 (BASF).

It is preferable to use the (poly)alkoxylated fatty acid esters in a proportion from 0.1 to 10 wt. %, preferably from 0.5 to 9 wt. %, in particular preferably from 1.0 to 7.5 wt. % and more preferably from 1.5 to 5.0 wt. %, relative in each case to the total weight of the preparation.

The preparations according to the present specification may include certain hydrophilically modified silicones to have a positive effect on foam stability and color uptake. Preferred hydrophilically modified silicones include certain polyalkoxylated silicones.

Therefore, In one example, the preparation may additionally contain at least one silicone of the dimethicone copolyol type. Preferred silicones of the dimethicone copolyol type are silicones of formula (Si-1),

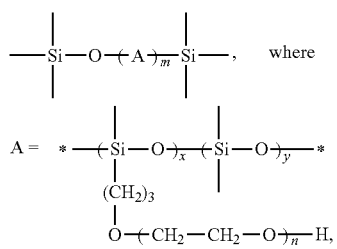

(Si-1)

in which "m" denotes an integer number from 1 to 1000,
"x" and "y" each independently of one another denote a number from 1 to 500, where, if m≥2, the values x and y in a structural element A can in each case be chosen independently from preceding structural elements A, and
"n" denotes a number from 1 to 50, preferably 3 to 30, more preferably 8 to 20, particularly preferably 10 to 15.

Examples of preferred and particularly suitable hydrophilically modified silicones include the compounds known under the INCI names PEG-12 Dimethicone (commercial name Dow Corning 193 C Fluid), PEG-17 Dimethicone (commercial product Silsoft 895 dimethicone copolyol), PEG-8 Dimethicone (Biowax liquid 754), PEG-10 Dimethicone (commercial products Dow Corning ES 5612 or Silsoft 860), PEG-14 Dimethicone (commercial product Abil B 8843).

In a particular example, the preparations may be characterized in that the silicone(s) of the dimethicone copolyol type is/are included in a proportion from 0.05 to 5.0 wt. %, preferably from 0.1 to 4.0 wt. %, in particular from 0.2 to 3.0 wt. % and particularly preferably from 0.3 to 2.0 wt. %, relative in each case to the total weight of the preparation.

The preparations may include additional active ingredients, auxiliary substances and additives, in particular further surfactants. As used in the present specification surfactants may refer to interfacially active substances, in particular anionic, amphoteric, zwitterionic, further non-ionic and cationic surfactants according to the definitions below.

Anionic surface-active substances which are suitable for use on the human body are suitable as anionic surfactants. These may be characterized by a water-solubilizing anionic group such as for example, a carboxylate, sulfate, sulfonate or phosphate group and a lipophilic alkyl group having approximately 8 to 30 C atoms. The molecule can additionally contain glycol or polyglycol ether groups, ester, ether and amide groups and hydroxyl groups. Examples of such anionic surfactants, in each case in the form of the sodium, potassium and ammonium and also the mono-, di- and trialkanolammonium salts having 2 to 4 C atoms in the alkanol group, are linear and branched fatty acids having 8 to 30 C atoms (soaps); ether carboxylic acids, in particular of the formula $RO(CH_2CH_2O)_xCH_2COOH$, in which R is a linear alkyl group having 8 to 30 C atoms and x=0 or 1 to 16; acyl sarcosides; acyl taurides; acyl isethionates; sulfosuccinic acid mono- and dialkyl esters and sulfosuccinic acid monoalkyl polyoxyethyl esters; linear alkane sulfonates; linear α-olefin sulfonates; sulfonates of unsaturated fatty acids; α-sulfofatty acid methyl esters of fatty acids; alkyl sulfates and alkyl ether sulfates, in particular of the formula $RO(CH_2CH_2O)_xSO_3H$, in which R denotes a linear alkyl group having 8 to 30 C atoms and x denotes 0 or a number from 1 to 12; mixtures of surface-active hydroxy sulfonates; sulfated hydroxyalkyl polyethylene and/or hydroxyalkylene propylene glycol ethers; esters of tartaric acid and citric acid with alcohols; alkyl and/or alkenyl ether phosphates of the formula $RO(C_2H_4O)_xP(=O)(OH)(OR')$, in which R denotes an aliphatic, optionally unsaturated hydrocarbon residue having 8 to 30 carbon atoms, R' denotes hydrogen, a residue —$(CH_2CH_2O)_yR$, and x and y independently of each other denote a number from 1 to 10; sulfated fatty acid alkylene glycol esters of the formula $RC(O)O(alkO)_nSO_3H$, in which R denotes a linear or branched, aliphatic, saturated and/or unsaturated alkyl residue having 6 to 22 C atoms, alk denotes —$CH_2CH_2$—, —$CH(CH_3)CH_2$— and/or —$CH_2CH(CH_3)$— and n denotes a number from 0.5 to 5; and monoglyceride sulfates and monoglyceride ether sulfates. Anionic surfactants that are preferred are soaps, alkyl sulfates, alkyl ether sulfates and ether carboxylic acids.

Surface-active compounds classed as zwitterionic surfactants may be those bearing at least one quaternary ammonium group and at least one carboxylate, sulfonate or sulfate group in the molecule. Examples of such zwitterionic surfactants are the betaines such as N-alkyl-N,N-dimethylammonium glycinates, for example cocoalkyl dimethylammonium glycinate, N-acyl aminopropyl-N,N-dimethylammonium glycinates, for example cocoacylaminopropyl dimethylammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name Cocamidopropyl Betaine.

As used in the present specification and in the appended claims, amphoteric surfactants may be surface-active compounds which in addition to a $C_8$-$C_{24}$ alkyl or acyl group contain at least one free amino group and at least one —COOH or —$SO_3H$ group in the molecule and are capable of forming internal salts. Conventional amphoteric surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids, each having approximately 8 to 24 C atoms in the alkyl group. Amphoteric surfactants by way of example are N-cocoalkylaminopropionate, cocoacylaminoethyl aminopropionate, $C_{12}$-$C_{18}$ acyl sarcosine and in particular the surfactant known under the INCI name Disodium Cocoamphodipropionate.

Further non-ionic surfactants and emulsifiers contain as the hydrophilic group a polyol group, a polyalkylene glycol ether group or a combination of polyol and polyglycol ether group, for example. In addition to the non-ionic surfactants already described, such compounds are for example the addition products of 1 to 50 mol of ethylene oxide and/or 0 to 5 mol of propylene oxide with linear and branched fatty alcohols having 8 to 30 C atoms, with fatty acids having 8 to 30 C atoms and with alkyl phenols having 8 to 15 C atoms in the alkyl group; addition products of 1 to 50 mol of ethylene oxide and/or 0 to 5 mol of propylene oxide with linear and branched fatty alcohols having 8 to 30 C atoms, with fatty acids having 8 to 30 C atoms and with alkyl phenols having 8 to 15 C atoms in the alkyl group, end-capped with a methyl or $C_2$ to $C_6$ alkyl residue, such as for example the types available under the commercial names Dehydrol LS, Dehydrol LT (BASF); polyglycerol esters and alkoxylated polyglycerol esters, such as for example poly(3)glycerol diisostearate (commercial product: Lameform TGI (Henkel)) and poly(2)glycerol polyhydroxystearate (commercial product: Dehymuls PGPH (Henkel)); polyol fatty acid esters, such as for example the commercial product Hydagen HSP (BASF) or Sovermol types (BASF); more highly alkoxylated, propoxylated and in particular ethoxylated, mono- and diglycerides having a degree of alkoxylation of greater than 5, such as for example glycerol monolaurate+20 ethylene oxide and glycerol monostearate+20 ethylene oxide; amine oxides; hydroxyl mixed ethers; sorbitan fatty acid esters and addition products of ethylene oxide with sorbitan fatty acid esters such as for example polysorbates and sorbitan monolaurate+20 ethylene oxide (EO); sugar fatty acid esters and addition products of ethylene oxide with sugar fatty acid esters; addition products of ethylene oxide with fatty acid alkanol amides and fatty amines; fatty acid-N-alkyl glucamides; alkyl phenols and alkyl phenol alkoxylates having 6 to 21, in particular 6 to 15 carbon atoms in the alkyl chain and 5 to 30 ethylene oxide and/or propylene oxide units.

As used in the present specification and in the appended claims, the term "non-ionic emulsifiers" may include the polymerization products of ethylene oxide and propylene oxide with saturated or unsaturated fatty acid esters of polyhydric alcohols with saturated or unsaturated fatty acids; alkyl esters of saturated or unsaturated fatty acids or alkyl phenols and alkoxylates thereof; in particular ethylene glycol ethers of fatty alcohols; mixed ethylene and propylene glycol ethers with fatty alcohols; fatty acid esters with sorbitan and polyethylene glycol; esters of non-hydroxylated $C_6$-$C_{30}$ alkyl monocarboxylic acids with polyethylene glycol; and addition products of alkyl phenols with ethylene oxide and/or propylene oxide.

As used in the present specification and in the appended claims, the term "cationic surfactants" may include monomeric quaternary ammonium compounds, esterquats and amidoamines. Preferred quaternary ammonium compounds are ammonium halides, in particular chlorides and bromides, such as alkyltrimethylammonium chlorides, dialkyldimethylammonium chlorides and trialkylmethylammonium chlorides, as well as the imidazolium compounds known under the INCI names Quaternium-27 and Quaternium-83. Further examples of cationic surfactants include the quaternized protein hydrolysates. Alkylamidoamines may be produced by amidation of natural or synthetic fatty acids and fatty acid cuts with dialkyl amino amines, such as stearamidopropyl dimethylamine. Likewise preferred esterquats may be quaternized ester salts of fatty acids with triethanolamine, quaternized ester salts of fatty acids with diethanol alkyl amines and quaternized ester salts of fatty acids with 1,2-dihydroxypropyl dialkylamines. Such products may be sold under the trademarks Stepantex®, Dehyquart® and Armocare®, for example. The products Armocare® VGH-70, an N,N-bis(2-palmitoyloxyethyl)dimethylammonium chloride, as well as Dehyquart® F-75, Dehyquart® C-4046, Dehyquart® L80 and Dehyquart® AU-35 are examples of such esterquats.

The preparations may contain further active ingredients, auxiliary substances and additives, for example non-ionic polymers, such as vinyl pyrrolidinone/vinyl acrylate copolymers, polyvinyl pyrrolidinone, vinyl pyrrolidinone/vinyl acetate copolymers, polyethylene glycols and polysiloxanes; silicones such as volatile or non-volatile, straight-chain, branched or cyclic, crosslinked or uncrosslinked polyalkyl siloxanes (such as dimethicones or cyclomethicones), polyaryl siloxanes and/or polyalkylaryl siloxanes, in particular polysiloxanes having organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers; anionic polymers, such as acrylic acid homo- and copolymers, xanthan, sodium carboxymethylcellulose; cationic or amphoteric polymer compounds are selected from Polyquaternium-2, Polyquaternium-6, Polyquaternium-7, Polyquaternium-10, Polyquaternium-11, Polyquaternium-16, Polyquaternium-22, Polyquaternium-28, Polyquaternium-32, Polyquaternium-37, Polyquaternium-39, Polyquaternium-44, Polyquaternium-46, Polyquaternium-55 and/or Polyquaternium-68; structuring agents such as glucose, maleic acid and lactic acid, hair-conditioning compounds such as phospholipids, for example lecithin and cephalins; perfume oils, dimethyl isosorbide and cyclodextrins; active ingredients to improve the fiber structure, in particular mono-, di- and oligosaccharides such as for example glucose, galactose, fructose, fruit sugars and lactose; dyes for coloring the agent; amino acids and oligopeptides, in particular arginine and/or serine; protein hydrolysates of animal and/or plant origin, such as for example elastin, collagen, keratin, silk and milk protein hydrolysates, or almond, rice, pea, potato and wheat protein hydrolysates, as well as those in the form of their fatty acid condensation products or optionally anionically or cationically modified derivatives thereof; vegetable oils, such as macadamia nut oil, palm oil, amaranth seed oil, peach kernel oil, avocado oil, olive oil, coconut oil, rapeseed oil, sesame oil, jojoba oil, soybean oil, groundnut oil, evening primrose oil and tea tree oil; light stabilizers; active ingredients such as panthenol, pantothenic acid, pantolactone, allantoin, pyrrolidinone carboxylic acids and salts thereof as well as bisabolol; polyphenols, in particular hydroxycinnamic acids, 6,7-dihydroxycoumarins, hydroxybenzoic acids, catechins, tannins, leukoanthocyanidins, anthocyanidins, flavanones, flavones and flavonols; ceramides or pseudoceramides; vitamins, provitamins and vitamin precursors, in particular from groups A, $B_3$, $B_5$, $B_6$, C, E, F and H; plant extracts; fats and waxes such as fatty alcohols, beeswax, montan wax and paraffins; swelling and penetrating substances such as glycerol, propylene glycol monoethyl ether, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate and PEG-3 distearate as well as pigments.

These further substances may be selected in accordance with the desired properties of the agents.

In some examples, the presence of propellants, in particular propellant gases, may form particularly stable, creamy, long-lasting foam preparations.

Therefore, in one example the preparation additionally contains at least one propellant.

Examples of preferred propellants include propellant gases, such as chlorofluorocarbons (CFCs) or hydrochlorofluorocarbons (HCFCs), compressed nitrogen, $N_2O$, $CO_2$, dimethyl ethers, propane and butane, in particular short-chain alkanes such as propane, butane or mixtures thereof.

The proportion of propellants in the preparations may dependent on the desired amount of foam. It is mostly between 1 and 10 wt. %, preferably between 3 and 8 wt. %, relative to the total weight of the preparation.

If propellant gas is added, the preparation may take the form of a foam. As used in the present specification and in the appended claims "a foam" may refer to a gas-liquid mixture. A foam indicates a structure consisting of gas-filled spherical or polyhedral cells (pores), which are delimited by liquid, semi-liquid or highly viscous cell walls. The foam preferably contains the propellant gases as the gas.

The proportion of gas in the foam is preferably at least 50 vol. %, preferably at least 70 vol. % and more preferably at least 80 vol. %, relative in each case to the total volume of the ready-to-use agent.

If the concentration by volume of the gas forming the foam is less than 74% in a homodisperse distribution, the gas bubbles may be spherical because of the surface-reducing action of the interfacial surface tension. Above the limit of the densest spherical packing the bubbles may be deformed into polyhedral lamellae, which may be delimited by a thin skin of approx. 4 to 600 nm. The cell walls, which are joined by node points, form a cohesive structure. The foam lamellae stretch between the cell walls (closed-cell foam). If the foam lamellae are destroyed or if they flow back into the cell walls at the end of foam production, an open-cell foam may be obtained.

Foams that are particularly suitable may have a gas-liquid ratio from 5 to 50 ml/g, preferably 10 to 40 ml/g and in particular 15 to 35 ml/g. Such a gas-liquid ratio is determined by measuring the volume of foam, using a measuring cylinder for example, for a known weight of the preparation, on completion of the mixing process, at room temperature and after a rest time of 1 minute. Alternatively, a certain volume can be removed, by dispensing it into a measuring cylinder for example, and its weight measured.

It may be particularly preferable for the color-changing preparation to have a low-viscosity formulation. Consolidated mixtures having a viscosity from 0 to 2000 mPa·s (measured at 22° C. in a Brookfield RV-T viscometer with an LV-1 or RV-1 spindle and a speed of 30 rpm) may be particularly preferable. A viscosity from 0 to 1000 mPa·s, measured under the stated conditions, is particularly preferred. A viscosity from 5 to 500 mPa·s, in particular from 10 to 50 mPa·s (measured in each case under the aforementioned conditions) is most particularly preferred.

For color-changing purposes the preparation may preferably additionally contain hydrogen peroxide as an oxidizing agent. Hydrogen peroxide or the addition products thereof with urea, melamine and sodium borate are suitable. The preparation particularly preferably contains hydrogen peroxide itself as the oxidizing agent.

The ready-to-use agent preferably contains the oxidizing agent, in particular hydrogen peroxide, in a proportion from 0.5 to 18 wt. %, in particular 1 to 15 wt. % and particularly preferably from 2 to 12 wt. %, relative in each case to the total weight of the preparation.

For stability reasons the hydrogen peroxide and the color-changing agent may be brought into contact with one another immediately before the application or during the application. To this end it may be preferable to provide the preparation and the oxidizing agent preparation, containing hydrogen peroxide, separately and to mix the oxidizing agent preparation with the preparation before or during the application.

To stabilize the hydrogen peroxide during storage it is preferable in particular if this oxidizing agent preparation has an acid pH before mixing, in particular between 2.5 and 5.5, preferably between 3.0 and 5.0. Preferred acidifying agents may include food acids, such as for example citric acid, acetic acid, malic acid or tartaric acid, as well as dilute mineral acids.

To stabilize hydrogen peroxide in the oxidizing agent preparation it may be preferable to use complexing agents. As used in the present specification and in the appended claims, the term "complexing agents" may refer to substances that are capable of complexing metal ions. Examples of preferred complexing agents are chelating agents, in other words substances which form cyclic compounds with metal ions, wherein an individual ligand occupies more than one coordination site on a central atom. The number of bonded ligands is dependent on the coordination number of the central ion. Examples of chelating agents may include polyoxycarboxylic acids, polyamines, ethylenediaminetetraacetic acid (EDTA), nitrilotriacetic acid (NTA) and hydroxyethane diphosphonic acids or the alkali salts thereof. Complexing agents that are preferred may include phosphonates, preferably hydroxyalkane or aminoalkane phosphonates, and in particular 1-hydroxyethane-1,1-diphosphonate (HEDP) or the disodium or tetrasodium salt thereof and/or ethylenediamine tetramethylene phosphonate (EDTMP) or the hexasodium salt thereof and/or diethylenetriamine pentamethylene phosphonate (DTPMP) or the heptasodium or octasodium salt thereof. Dipicolinic acid is also preferably used as the complexing agent. Agents containing a combination of an EDTA salt, HEDP and dipicolinic acid are particularly preferred.

The ready-to-use preparation has an alkaline pH of preferably between 7 and 12, preferably between 8 and 11.5 and in particular between 8.5 and 11.0. The pH may be adjusted using pH adjusters. Examples of acidifying and alkalizing agents include those used in cosmetics for adjusting the pH.

The color-changing preparation may therefore preferably additionally contain at least one alkalizing agent. The alkalizing agents of the alkalizing preparation may be chosen from inorganic salts, in particular alkali and alkaline-earth metals, organic alkalizing agents, in particular amines, basic amino acids and alkanol amines, and ammonia.

Organic alkalizing agents for use are preferably selected from alkanol amines. Alkanol amines are primary, secondary or tertiary amines having a $C_2$-$C_6$ alkyl parent substance bearing at least one hydroxyl group. Alkanol amines that are preferred according to the invention are selected from triethanolamine, 2-aminoethan-1-ol (monoethanolamine), 2-amino-2-methylpropan-1-ol and 2-amino-2-methylpropane-1,3-diol. A particularly preferred alkanol amine is monoethanolamine. Suitable basic amino acids are for example lysine, arginine and ornithine. Inorganic alkalizing agents according to the invention are preferably selected from the group formed from sodium hydroxide, potassium hydroxide, calcium hydroxide, barium hydroxide, sodium phosphate, potassium phosphate, sodium silicate, sodium metasilicate, potassium silicate, ammonium carbonate, sodium carbonate and potassium carbonate.

The alkalizing agent may be present in the color-changing preparation in a sufficient quantity to give the ready-to-use agent an alkaline pH, preferably from 8 to 12, after mixing with the oxidizing agent preparation. Color-changing preparations may preferably contain the alkalizing agent(s) in a proportion from 1 to 25 wt. %, in particular 2 to 15 wt. %, preferably 2.5 to 10 wt. %, relative in each case to the total weight of the color-changing preparation.

If the preparation contains a propellant, in particular a propellant gas, it may be preferably stored in a pressure-resistant container. For packaging reasons the oxidizing agent preparation may be applied at the same time as the preparation. To this end the oxidizing agent preparation may likewise contain at least one propellant, preferably a propellant gas, as specified above. In this way the oxidizing agent preparation is also dispensed as a foam, preferably with the aforementioned specifications for foam.

The preparation containing additionally at least one propellant, and the oxidizing agent preparation containing at least one propellant, may be either applied at the same time from two different containers or may be preferably dispensed from a double-chamber container having two pressure-resistant storage vessels with one common or two separate outlets. If it has two outlets, they are preferably both opened and closed by means of a common operating element.

The present specification also provides a method for changing the color of keratinic fibers, which is characterized in that:

(i) a preparation according to a present specification, additionally including at least one propellant; and an oxidizing agent preparation, containing in a cosmetic carrier, the oxidizing agent preparation including at least one oxidizing agent and a propellant, are discharged onto the fibers together and at the same time.

(ii) The preparation and oxidizing agent preparation may be mixed together thoroughly on the fibers and are distributed evenly on the fibers.

(iii) The preparation and the oxidizing agent preparation may be rinsed out of the fibers after a contact time of 10 to 45 min at a temperature of 20 to 45° C.

In the first process step (i) the preparation and the oxidizing agent preparation are dispensed together and at the same time onto the keratinic fibers. To this end the preparation and the oxidizing agent preparation may be in separately packaged, preferably pressure-resistant storage vessels. The vessels may have a manual valve as an outlet for each preparation, preferably operable with a finger. Double-chamber containers, each chamber having an outlet valve, are preferably used. The container may be opened or closed by means of the outlet valve. The two outlet valves are particularly preferably controlled by means of a common operating element, such that the two valves are either both open or both closed. This ensures that the two agents are dispensed onto the fibers together and at the same time. The amounts of the preparation and the oxidizing agent preparation may be adapted to one another by adjusting the size of the valves and adjusting the pressure in the two storage vessels. The preparation and the oxidizing agent preparation may be dispensed from the containers via the outlet valves.

The preparation and the oxidizing agent preparation may either be dispensed side by side from two different outlet channels without being mixed or dispensed from a common outlet channel with at least partial mixing. The outlet channels can have additional mechanical aids for adjusting the foam properties, such as meshes with particular pore sizes.

Such double-chamber containers may be obtained for example from TOYO® Aerosol Industry Co. Ltd.

In the second process step (ii) the preparation and the oxidizing agent preparation may be mixed together by manually combining the preparation and the oxidizing agent preparation and the resulting mixture may be evenly distributed on the fibers. In a method for changing the color of human hair the ready-to-use agent may be dispensed, mixed and distributed directly on the user's hair. The distribution may also be preferably carried out manually, optionally also using further aids such as a comb or brush. Direct contact between the ready-to-use agents and the hands may be preferably avoided by using suitable gloves such as disposable gloves, made from latex for example.

In the third process step (iii) the ready-to-use agent remains on the fibers to be treated for a period from 10 to 45 minutes. The period is preferably between 20 and 40 minutes. The application temperature may be in a range between 20 and 45° C. During the time for which the agent remains on the fibers a higher or precisely defined temperature can optionally also be set using external heat sources. It is particularly preferable for the color change to be supported by physical measures. Methods according to the invention in which the application is supported by the action of heat, infrared and/or UV radiation during the contact time can be preferred.

After the contact time according to the third process step the remaining portions of the preparations may be removed from the fibers to be treated by rinsing. To this end the fibers may be rinsed with water and/or an aqueous surfactant preparation. Water heated to a temperature of 20° C. to 40° C. or a correspondingly heated aqueous surfactant preparation may be used for this purpose.

In order to carry out the method, the preparations and containers may be preferably presented in a packaging unit.

The present specification describes a packaging unit comprising a plurality of components (kit of parts), comprising (a) at least one first container which contains a preparation, additionally containing at least one propellant, and (b) at least one second container (II) which contains an oxidizing agent preparation containing in a cosmetic carrier at least one oxidizing agent and a propellant.

The separately packaged preparation and oxidizing agent preparation may be provided in physically separate containers. As used in the present specification and in the appended claims, the term "container" may denote a holding possibility, regardless of its shape, material or closure, which is capable of containing substances or mixtures of substances. The term "container" thus may include, without being limited thereto, the inside of a tube, pouch or bag, canister, can, tub, bottle, jar, pack, carton, box, envelope or other vessel. The components of the preparations can be contained in a single container having a plurality of compartments for holding the preparations, but it is also possible and optionally preferable to divide them between different containers.

It is particularly preferred if the first containers and second containers each constitute a storage vessel of a double-chamber container described above, in which the outlet valves of the storage vessels can be controlled by means of a common operating element.

In a preferred example of the packaging unit comprising a plurality of components, the first containers and second containers each have a valve as an outlet, characterized in that the valves of the two containers can be opened and closed manually at the same time by means of a common operating element.

The common operating element may be preferably a button- or pushbutton-type unit which, when pressure is exerted on it, in particular with a finger, opens both valves of the containers at the same time and then closes them at the same time when the pressure is removed.

All that has been stated in respect of the methods and preparations applies with necessary alterations to further preferred embodiments of the kit according to the invention.

EXAMPLES

The following preparations were produced. Unless otherwise specified, the stated quantities are percentages by weight. Table 1a below indicates a number of ingredients used in a number of color-changing preparations (C1, C2, E1, E2) according to the present specification.

TABLE 1a

| Raw materials | C1 | C2 | E1 | E2 |
|---|---|---|---|---|
| Plantacare 818 UP | 5.00 | 5.00 | 5.00 | 5.00 |
| Dimethylcocoylbetaine | 5.00 | 5.00 | 5.00 | — |
| Cremophor CO 60 | 2.00 | 2.00 | 2.00 | — |
| Potassium oleate | — | 2.60 | 2.60 | 3.75 |
| Comperlan 100 | — | — | 1.50 | 2.00 |
| Dow Corning 193 C Fluid | — | — | — | 0.50 |
| Ethanol, 96% | 5.00 | 5.00 | 5.00 | 0.50 |
| EDTA | 0.20 | 0.20 | 0.20 | — |
| p-Toluylenediamine | 1.35 | 1.35 | 1.35 | 1.35 |

TABLE 1a-continued

| Raw materials | C1 | C2 | E1 | E2 |
|---|---|---|---|---|
| sulfate | | | | |
| 4-Chlororesorcinol | 0.06 | 0.06 | 0.06 | 0.06 |
| 3-Aminophenol | 0.02 | 0.02 | 0.02 | 0.02 |
| 5-Amino-2-methylphenol | 0.72 | 0.72 | 0.72 | 0.72 |
| Ascorbic acid | 0.05 | 0.05 | 0.05 | — |
| Sodium sulfite, anhydrous | 0.20 | 0.20 | 0.20 | — |
| L-Serine | 1.00 | 1.00 | 1.00 | — |
| Merquat 281 | 3.00 | 3.00 | 3.00 | — |
| Monoethanolamine | 6.00 | 6.00 | 6.00 | 4.00 |
| Perfume | | | qs | |
| Water | | | to 100 | |

Table 1b below indicates a number of ingredients used in a number of color-changing preparations (E3, E4, E5, E6) according to the present specification.

TABLE 1b

| Raw materials | E3 | E4 | E5 | E6 |
|---|---|---|---|---|
| Potassium oleate, 12.5% | 1.60 | 1.60 | 16.0 | 16.0 |
| Plantacare 818 UP | 10.00 | — | 10.00 | — |
| Cremophor CO 60 | 4.00 | — | 4.00 | — |
| Comperlan 100 | 1.50 | 2.00 | 1.50 | 2.00 |
| Dow Corning 193 C Fluid | 1.00 | — | 1.00 | — |
| Cetrimonium bromide | — | 3.00 | — | 3.00 |
| Phospholipid EFA | — | 1.50 | — | 1.50 |
| Ethanol, 96% | 5.00 | — | 5.00 | — |
| HEDP, 60% | 0.20 | — | 0.20 | — |
| Potassium hydroxide, 50% | 0.50 | 0.50 | 0.50 | 0.50 |
| p-Toluylenediamine sulfate | 1.80 | 1.80 | 1.80 | 1.80 |
| 1-(2-Hydroxyethyl)-4,5-diaminopyrazole sulfate | 0.50 | 0.50 | 0.50 | 0.50 |
| 2-Methylresorcinol | 0.45 | 0.45 | 0.45 | 0.45 |
| 3-Aminophenol | 0.18 | 0.18 | 0.18 | 0.18 |
| 4-Chlororesorcinol | 0.02 | 0.02 | 0.02 | 0.02 |
| 2-Amino-3-hydroxypyridine | 0.40 | 0.40 | 0.40 | 0.40 |
| Resorcinol | 0.02 | 0.02 | 0.02 | 0.02 |
| 5-Amino-2-methylphenol | 0.25 | 0.25 | 0.25 | 0.25 |
| 2-Amino-6-chloro-4-nitrophenol | 0.20 | 0.20 | 0.20 | 0.20 |
| HC Blue No. 12 | 0.03 | 0.03 | 0.03 | 0.03 |
| Ascorbic acid | 0.05 | — | 0.05 | — |
| Sodium sulfite | 0.20 | — | 0.20 | — |
| L-Serine | 1.00 | — | 1.00 | — |
| Monoethanolamine | 6.00 | — | 6.00 | — |
| Perfume | qs | qs | qs | qs |
| Water | to 100 | to 100 | to 100 | to 100 |

Table 2 below indicates an oxidizing agent preparation (OX-1) ingredient list according to the present specification.

TABLE 2

| Raw material | OX-1 |
|---|---|
| Sodium hydroxide solution, 45% | 0.73 |
| Dipicolinic acid | 0.1 |
| Disodium pyrophosphate | 0.03 |
| HEDP, 60% | 1.5 |
| Plantacare 818 UP | 5.0 |
| Cremophor CO 60 | 2.0 |
| Eumulgin L | 0.4 |
| Hydrogen peroxide (aqueous, 50%) | 15.0 |
| Water | to 100 |

Table 3 below presents a number of commercial products available for use in the preparation, oxidizing agent preparation or combinations thereof.

TABLE 3

| | |
|---|---|
| Cremophor CO 60 | INCI name: PEG-60 Hydrogenated Castor Oil (BASF) |
| Comperlan 100 | approx. 92-99% active substance content; INCI name: Cocamide MEA (BASF) |
| Plantacare 818 UP | approx. 51-53% active substance content; INCI name: Coco-Glucoside, Aqua (Water) (BASF) |
| Dow Corning 193 C Fluid | INCI name: PEG-12 Dimethicone (Dow Corning) |
| Merquat 281 | approx. 39-43% active substance content; INCI name: Polyquaternium-22, Aqua (Water) (Nalco) |
| Eumulgin L | INCI name: PPG-1-PEG-9 Lauryl Glycol Ether (BASF) |
| Phospholipid EFA | approx. 30% active substance; INCI name: Linoleamidopropyl PG-dimonium Chloride Phosphate, water (45%), propylene glycol (25%) (Uniqema) |

Pigment Removal

In one example, the color-changing preparations C1, C2, E1 to E4 and the oxidizing agent preparation OX-1 were each mixed with a propellant gas mixture of propane/butane (1:1) in the ratio 95:5 in a pressure-resistant container.

The color-changing preparations C1 and C2 as well as E1 to E4 were each applied together with the oxidizing agent OX-1 from the storage containers ("containers") of a double-chamber container having a common operating element for the outlet valves of the storage containers to strands of hair (buffalo belly hair/BB or Euronaturhaar/ENH, Kerling, white) in the ratio 1:1, and the preparations were mixed together by combining them thoroughly on the fibers. The application mixture remained on the hair for a contact time of 30 minutes at room temperature. Then the remaining agent was rinsed out of the hair for approximately 2 minutes using tepid water and the hair was dried with a towel.

Colorimetric measurements were performed on the strand at four measuring points in each case. A Spectralflash SF 450 from Datacolor was used as the measuring instrument.

The results of the measurements were quantified by means of the CIELAB color space.

The "L" value represents the lightness of the color (black-white axis); the higher the "L" value, the lighter the color. The "a" value represents the red-green axis of the system; the higher the value, the greater the shift to the red. The "b" value represents the yellow-blue axis of the system; the higher the value, the greater the shift to the yellow. Color differences are characterized by the ΔE value:

$$\Delta E = \sqrt{(L^*_1 - L^*_2)^2 + (a^*_1 - a^*_2)^2 + (b^*_1 - b^*_2)^2}$$

The following coloring results were obtained (Table 4):

TABLE 4

| Hair type | Recipe | L* | a* | b* | ΔE |
|---|---|---|---|---|---|
| BB | untreated | 72.98 | 2.27 | 22.57 | |
| BB | C1 | 30.37 | 14.02 | −3.04 | 51.1 |
| BB | C2 | 24.83 | 13.42 | −2.76 | 55.5 |
| BB | E1 | 22.69 | 12.78 | −3.92 | 57.8 |
| BB | E2 | 22.61 | 13.32 | −4.09 | 58.1 |
| ENH | untreated | 72.68 | −0.23 | 8.78 | |
| ENH | C1 | 25.88 | 15.29 | −7.06 | 51.8 |
| ENH | C2 | 25.68 | 14.62 | −6.71 | 51.7 |
| ENH | E1 | 21.42 | 13.86 | −6.34 | 55.3 |
| ENH | E2 | 19.57 | 12.48 | −5.67 | 56.5 |

The use of the coloring preparations E1 and E2 led to a marked improvement in the color intensity (ΔE value) of the coloring on both hair types as compared with the preparations C1 (without soap and without non-ionic surfactant according to formula (I)) and C2 (without non-ionic surfactant according to formula (I)). Preparations C1 and C2 are not preparations according to the present specification.

Even, long-lasting and glossy colors having high color intensity and chromaticity were obtained.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A preparation for changing the color of keratinic fibers, containing, in a cosmetically acceptable carrier:
    at least one color-changing agent;
    at least one soap;
    at least one non-ionic surfactant of formula (I),

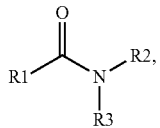

(I)

in which:
    R1 denotes an alkyl or alkenyl residue having 5 to 21 carbon atoms;
    R2 denotes a C2-C4 monohydroxyalkyl residue; and
    R3 denotes hydrogen, a C1-C4 alkyl residue or a C2-C4 monohydroxyalkyl residue; and
    at least one propellant;
wherein:
    the preparation is in the form of a foam; and
    a proportion of gas in the foam is at least 50% by volume.

2. The preparation of claim 1, in which the at least one soap is an alkali metal salt of an unsaturated and/or branched fatty acid having 8 to 22 carbon atoms.

3. The preparation of claim 1, in which the at least one soap is an alkali metal salt of oleic acid.

4. The preparation of claim 1, in which the at least one soap is included in a proportion from 0.1 to 6 wt. % of the total weight of the preparation.

5. The preparation of claim 1, in which:
    R2 of formula (I) denotes 2-hydroxyethyl ($CH_2CH_2OH$); and
    R3 of formula (I) denotes hydrogen.

6. The preparation of claim 1, in which the compound of formula (I) is cocamide MEA.

7. The preparation of claim 1, in which the at least one non-ionic surfactant is included in a proportion from 0.1 to 10 wt. % of the total weight of the preparation.

8. The preparation of claim 1, in which the at least one soap and the at least one non-ionic surfactant of formula (I) are included in a weight ratio between 8/1 and 1/3.

9. The preparation of claim 6, further comprising potassium oleate and lauramide MEA.

10. The preparation of claim 9, in which the potassium oleate and cocamide MEA are included in a weight ratio between 8/1 to 1/3.

11. The preparation of claim 1, further comprising at least one additional non-ionic surfactant, selected from alkyl polyglucosides and/or alkoxylated fatty acid esters.

12. A method for changing the color of keratinic fibers, the method comprising:
    applying to the fibers at the same time a preparation and an oxidizing agent preparation, in which:
    the preparation comprises:
        at least one color-changing agent;
        at least one soap;
        at least one propellant; and
        at least one non-ionic surfactant of formula (I),

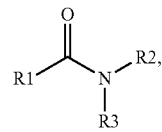

(I)

in which:
    R1 denotes an alkyl or alkenyl residue having 5 to 21 carbon atoms;
    R2 denotes a $C_2$-$C_4$ monohydroxyalkyl residue; and
    R3 denotes hydrogen, a $C_1$-$C_4$ alkyl residue or a $C_2$-$C_4$ monohydroxyalkyl residue; and
the oxidizing agent preparation comprises, in a cosmetic carrier:
    at least one oxidizing agent; and
    a propellant;
distributing the preparation and the oxidizing agent preparation uniformly over the fibers; and
rinsing the preparation and the oxidizing agent preparation out of the fibers after a contact time of 10 to 45 min at a temperature of 20 to 45° C.;
wherein the at least one soap and the at least one non-ionic surfactant of formula (I) are included in a weight ratio between 8/1 and 1/3.

13. A packaging unit comprising:
at least one first container which contains a preparation that comprises:
    at least one color-changing agent;
    at least one soap;
    at least one propellant; and
    at least one non-ionic surfactant of formula (I),

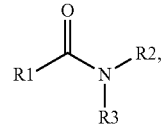

(I)

in which:
    R1 denotes an alkyl or alkenyl residue having 5 to 21 carbon atoms;
    R2 denotes a $C_2$-$C_4$ monohydroxyalkyl residue; and
    R3 denotes hydrogen, a $C_1$-$C_4$ alkyl residue or a $C_2$-$C_4$ monohydroxyalkyl residue; and at least one second container which contains an oxidizing agent preparation that comprises, in a cosmetic carrier:
at least one oxidizing agent; and
a propellant;
wherein:
a mixture of the preparation in the at least one first container and the preparation in the at least one second container is in the form of a foam; and
a proportion of gas in the foam is at least 50% by volume.

14. The packaging unit of claim 13, in which:
the at least one first container and the at least one second container each have a valve as an outlet; and
the valves of the containers are manually opened and closed at the same time by means of a common operating element.

15. The preparation of claim 8, in which R2 of formula (I) denotes 2-hydroxyethyl (—$CH_2CH_2OH$), and R3 of formula (I) denotes hydrogen.

16. The preparation of claim 8, further comprising at least one additional non-ionic surfactant, selected from alkyl polyglucosides and/or alkoxylated fatty acid esters.

17. The method of claim 12, wherein the preparation is in the form of a foam, and said foam comprises at least 50% by volume of gas.

18. The method of claim 12, in which:
the at least one soap comprises an alkali metal salt of oleic acid; and
the at least one non-ionic surfactant of formula (I) comprises lauramide MEA.

19. The packaging unit of claim 13, in which the at least one soap and the at least one non-ionic surfactant of formula (I) are included in the preparation in the at least one first container in a weight ratio between 8/1 and 1/3.

20. The packaging unit of claim 13, further comprising at least one additional non-ionic surfactant, selected from alkyl polyglucosides and/or alkoxylated fatty acid esters.

* * * * *